(12) United States Patent
Matsumura et al.

(10) Patent No.: US 11,672,458 B2
(45) Date of Patent: Jun. 13, 2023

(54) SENSOR, SENSOR MODULE, AND SENSOR HOUSING

(71) Applicant: Nihon Kohden Corporation, Tokyo (JP)

(72) Inventors: Fumiyuki Matsumura, Tokorozawa (JP); Norihito Konno, Tokorozawa (JP); Minori Hosoi, Tokorozawa (JP); Hirohiko Ikeya, Tokorozawa (JP)

(73) Assignee: Nihon Kohden Corporation, Tokyo (JP)

( * ) Notice: Subject to any disclaimer, the term of this patent is extended or adjusted under 35 U.S.C. 154(b) by 22 days.

(21) Appl. No.: 16/439,081

(22) Filed: Jun. 12, 2019

(65) Prior Publication Data

US 2019/0380614 A1 Dec. 19, 2019

(30) Foreign Application Priority Data

Jun. 13, 2018 (JP) .............................. JP2018-112860

(51) Int. Cl.
*A61B 5/00* (2006.01)
*A61B 5/24* (2021.01)
*A61B 5/259* (2021.01)
*A61B 5/274* (2021.01)

(52) U.S. Cl.
CPC .............. *A61B 5/259* (2021.01); *A61B 5/002* (2013.01); *A61B 5/274* (2021.01)

(58) Field of Classification Search
CPC ..... A61B 5/04085; A61B 5/259; A61B 5/002; A61B 5/274; A61B 5/256; A61B 5/28; A61B 5/282
See application file for complete search history.

(56) References Cited

U.S. PATENT DOCUMENTS

| | | | | |
|---|---|---|---|---|
| 8,214,007 | B2* | 7/2012 | Baker | A61B 5/0006 600/372 |
| 9,538,918 | B2* | 1/2017 | Russell | A61B 5/6833 |
| 10,555,683 | B2* | 2/2020 | Bahney | A61B 5/0408 |
| 2008/0139953 | A1 | 6/2008 | Baker et al. | |
| 2010/0081913 | A1* | 4/2010 | Cross | A61B 5/04085 600/386 |
| 2013/0274584 | A1* | 10/2013 | Finlay | A61B 5/0432 600/391 |

(Continued)

FOREIGN PATENT DOCUMENTS

| | | |
|---|---|---|
| JP | 2004-121360 A | 4/2004 |
| JP | 2017-506121 A | 3/2017 |
| JP | 2018-504148 A | 2/2018 |

OTHER PUBLICATIONS

Office Action dated Mar. 29, 2022, issued by the Japan Patent Office in counterpart Japanese Patent Machine Application No. 2018-112860.

*Primary Examiner* — Adam Z Minchella
(74) *Attorney, Agent, or Firm* — Sughrue Mion, PLLC

(57) ABSTRACT

A first electrode and a second electrode are attached to a subject. A processor module acquires physiological information of the subject based on biopotential that are detected by the first electrode and the second electrode, respectively. A housing has a battery housing member for housing a primary battery which supplies an electric power to the processor module. The processor module is attachable to and detachable from the housing.

12 Claims, 15 Drawing Sheets

(56) References Cited

U.S. PATENT DOCUMENTS

| | | | |
|---|---|---|---|
| 2014/0051946 A1* | 2/2014 | Arne | A61B 5/0006 455/414.1 |
| 2015/0094558 A1* | 4/2015 | Russell | G16H 40/67 600/386 |
| 2015/0238094 A1* | 8/2015 | Lai | A61B 5/0006 600/509 |
| 2016/0120433 A1 | 5/2016 | Hughes et al. | |
| 2016/0120434 A1 | 5/2016 | Park et al. | |
| 2017/0188872 A1* | 7/2017 | Hughes | A61B 5/366 |
| 2018/0132733 A1 | 5/2018 | Lai et al. | |
| 2018/0242876 A1 | 8/2018 | Hughes et al. | |
| 2019/0046066 A1 | 2/2019 | Hughes et al. | |
| 2019/0190293 A1* | 6/2019 | Wawro | A61N 1/3603 |
| 2019/0274574 A1 | 9/2019 | Hughes et al. | |
| 2020/0178828 A1* | 6/2020 | Bahney | A61B 5/25 |
| 2020/0289014 A1 | 9/2020 | Park et al. | |
| 2021/0217519 A1 | 7/2021 | Park et al. | |
| 2022/0093247 A1 | 3/2022 | Park et al. | |

\* cited by examiner

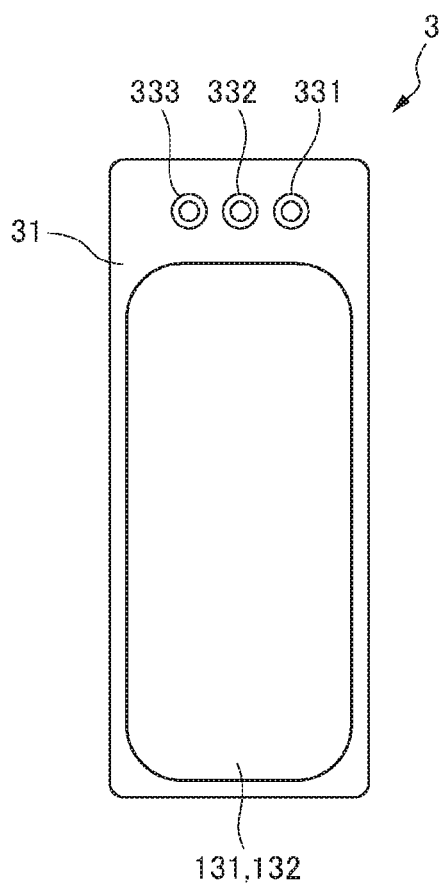
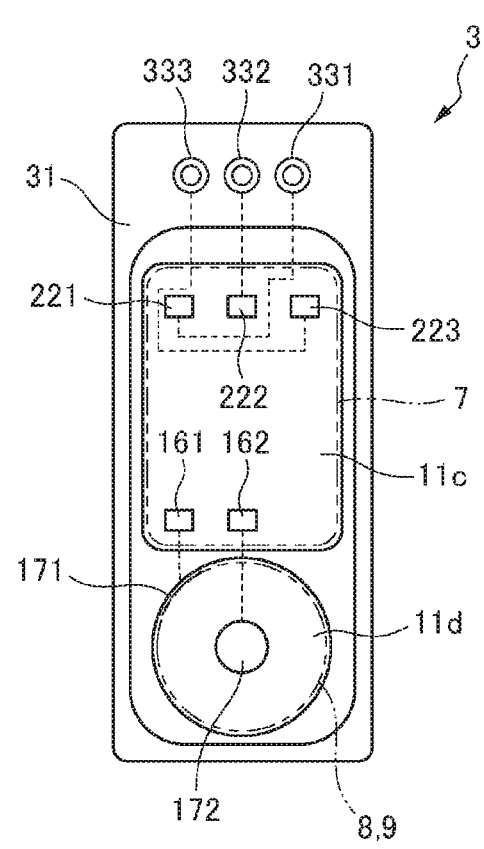

SENSOR, SENSOR MODULE, AND SENSOR HOUSING

CROSS-REFERENCE TO RELATED APPLICATIONS

This application is based on and claims priority under 35 USC 119 from Japanese Patent Application No. 2018-112860 filed on Jun. 13, 2018, the contents of which are incorporated herein by reference.

TECHNICAL FIELD

The presently disclosed subject matter relates to a sensor which is attached to a subject to acquire physiological information of the subject, and a sensor module and sensor housing which constitute the sensor.

BACKGROUND ART

As an example of such a sensor, Patent Literature 1 discloses a biopotential detection device. The biopotential detection device includes an electrode pad and a signal processor. The electrode pad supports electrodes. Gel members which are electrically conductive and adhesive are attached to the lower surface of the electrode pad so as to cover respectively the electrodes. Terminals which are parts of the electrodes are exposed from the upper surface of the electrode pad. The signal processor is detachably attached to the upper surface of the electrode pad. The signal processor includes connecting portions and a signal processing circuit. When the signal processor is attached to the electrode pad, the terminals are connected the connecting portions, respectively. This causes the electrodes and the signal processing circuit to be electrically connected to each other through the connecting portions.

The electrode pad is attached to the subject so that the lower surface is opposed to the biological surface. At this time, the gel members are in close with the biological surface (skin). A signal corresponding to the biopotential is taken out from the terminals through the gel members and the electrodes. The signal processing circuit of the signal processor performs a process for wirelessly transmitting the signal. The electric power which is required for performing the signal processing is supplied from a battery incorporated in the signal processor.

CITATION LIST

Patent Literature

Patent Literature 1: JP-A-2004-121360

SUMMARY OF INVENTION

In the biopotential detection device, the electrode pad is replaced with new one every subject, and the signal processor is attached to the new electrode pad to be reused. However, the use mode which the signal processor is allowed to perform is that the signal processor is attached to the electrode pad to acquire the biopotential corresponding to the chest lead in an electrocardiogram.

It is an object of the presently disclosed subject matter to provide a wide variety of modes of acquiring physiological information while suppressing the operational cost from being raised.

A first aspect for achieving the object is a sensor wherein the sensor includes:
a plurality of electrodes which are to be attached to a subject,
a processor module which acquires physiological information of the subject based on biopotential that are detected by the plurality of electrodes, respectively; and
a housing having a battery housing member for housing a battery which supplies an electric power to the processor module, and
the processor module is attachable to and detachable from housing In the case where, for example, an electrocardiogram is to be acquired as physiological information of the subject, the number of electrodes to be used, attaching position, and the configuration of the sensor housing are varied depending on the acquisition mode. However, the processing function in which physiological information is acquired based on biopotential that are acquired through the electrodes is approximately common to the varied configurations. When a configuration having the processing function is modularized, and the configuration is made attachable to and detachable from the sensor housing independently of the battery, therefore, a plurality of kinds of sensor housings can share the processor module. When the processor module is attached to a sensor housing that is suitable to a mode of acquiring physiological information to be obtained, it is possible to provide use environments for various sensors. Moreover, it is not necessary to dispose a processor for each of sensor housings, and therefore the operational cost can be suppressed from being raised.

Therefore, a second aspect for achieving the object is a processor module which acquires physiological information of a subject based on biopotential that are detected by a plurality of electrodes attached to the subject, respectively, wherein the processor module is attachable to and detachable from a housing having a battery housing member for housing a battery, and receives a power supply from the battery.

Moreover, a third aspect for achieving the object is a sensor housing having a battery housing member for housing a battery which supplies an electric power to a processor module for acquiring physiological information of a subject based on biopotential that are detected by a plurality of electrodes attached to the subject, wherein the processor module is attachable to and detachable from the sensor housing.

BRIEF DESCRIPTION OF DRAWINGS

FIGS. 14A and 14B illustrate the configuration of a housing of a sensor of a third embodiment.

DESCRIPTION OF EMBODIMENTS

Figure 1A:
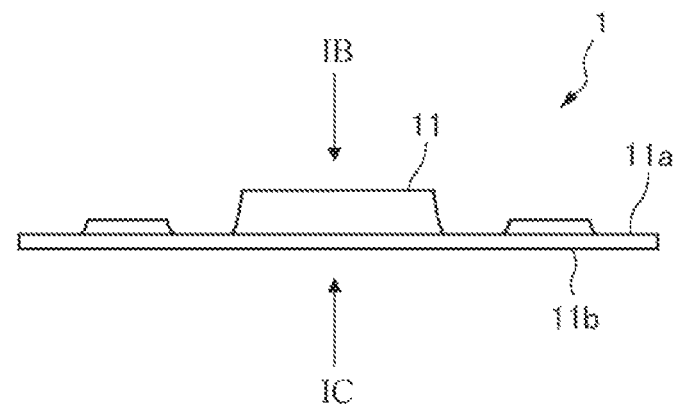
FIGS. 1A to 1C illustrate the appearance of a sensor of a first embodiment.

Hereinafter, embodiments will be described in detail with reference to the accompanying drawings. In the drawings, in order to make the components to be described; to have a recognizable size, their scales are appropriately changed. The terms "upper" and "lower" in the specification are merely used for convenience of description of the structure, and it is not intended by the terms to limit the attitude in a use of the structure.

Figure 1B:
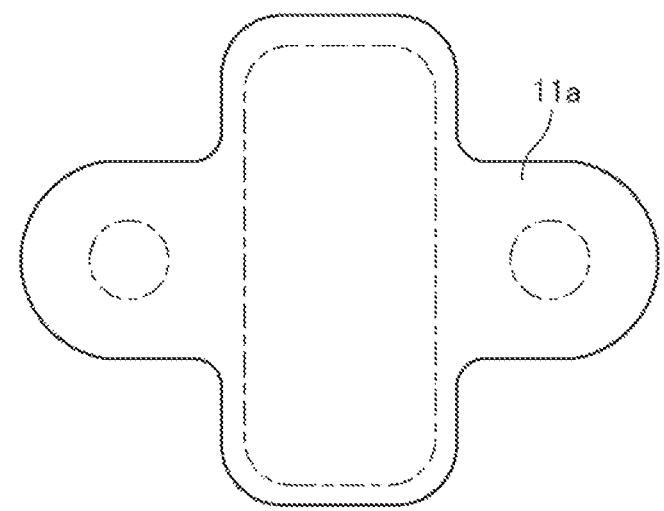
Figure 1C:
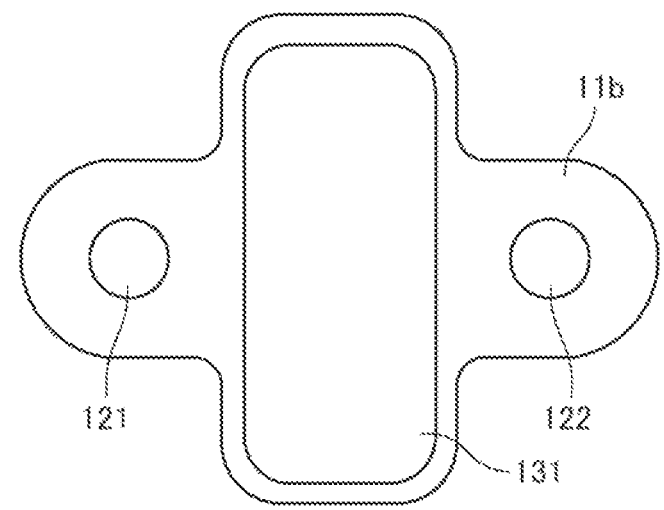

FIG. 1A illustrates the appearance of a sensor 1 of a first embodiment, FIG. 1B illustrates the appearance of the sensor 1 as seen in the direction of the arrow IB in FIG. 1A, and FIG. 1C illustrates the appearance of the sensor 1 as seen in the direction of the arrow IC in FIG. 1A.

The sensor 1 may include a housing 11. The housing 11 may include an upper surface 11a and a lower surface 11b.

The sensor 1 may include a first electrode 121 and a second electrode 122. The first electrode 121 and the second electrode 122 are electrically conductive. The first electrode 121 and the second electrode 122 are supported by the housing 11. The first electrode 121 and the second electrode 122 are exposed from the lower surface 11b of the housing 11.

Figure 2:
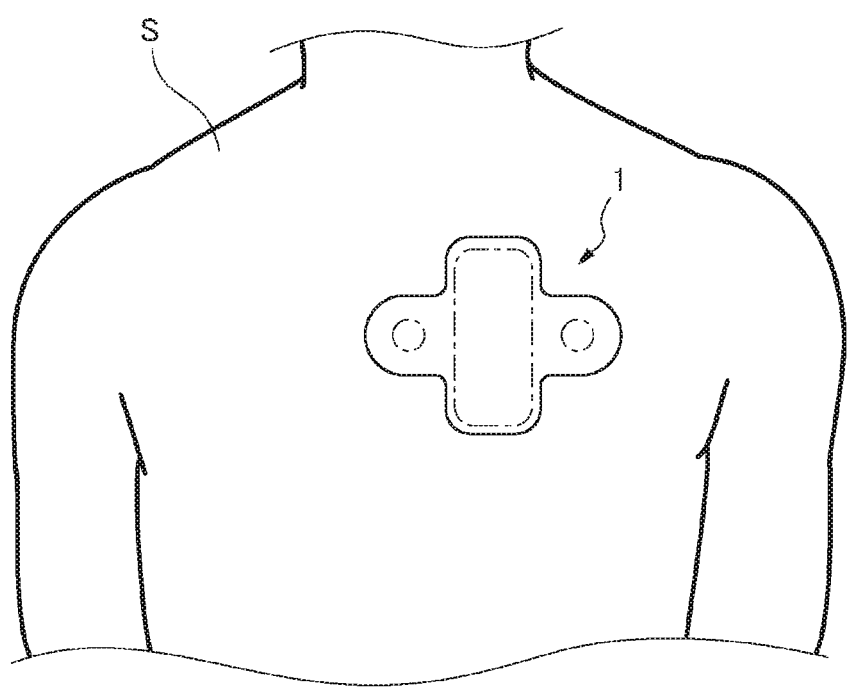
FIG. 2 illustrates a position where the sensor of FIG. 1A is attached.

As illustrated in FIG. 2, the sensor 1 is attached to the chest of a subject S. At this time, the lower surface 11b of the housing 11 is opposed to the skin of the subject S. Specifically, a gel member which is electrically conductive and adhesive, and which is not illustrated is attached to the lower surface 11b so as to cover at leak the first electrode 121 and the second electrode 122. This causes the sensor 1 to be held on the skin of the subject S. The first electrode 121 and the second electrode 122 detect biopotential of the subject S at their positions, respectively.

In the following description, the term "attached to the subject" which is mainly used in relation to the electrodes means both a case where the electrodes are directly attached to the skin of the subject, and that where the electrodes are attached to the skin of the subject via the gel member or the like.

As illustrated in FIG. 1C, the sensor 1 may include a first cover 131. The first cover 131 is disposed on the lower surface 11b of the housing 11.

Figure 3A:
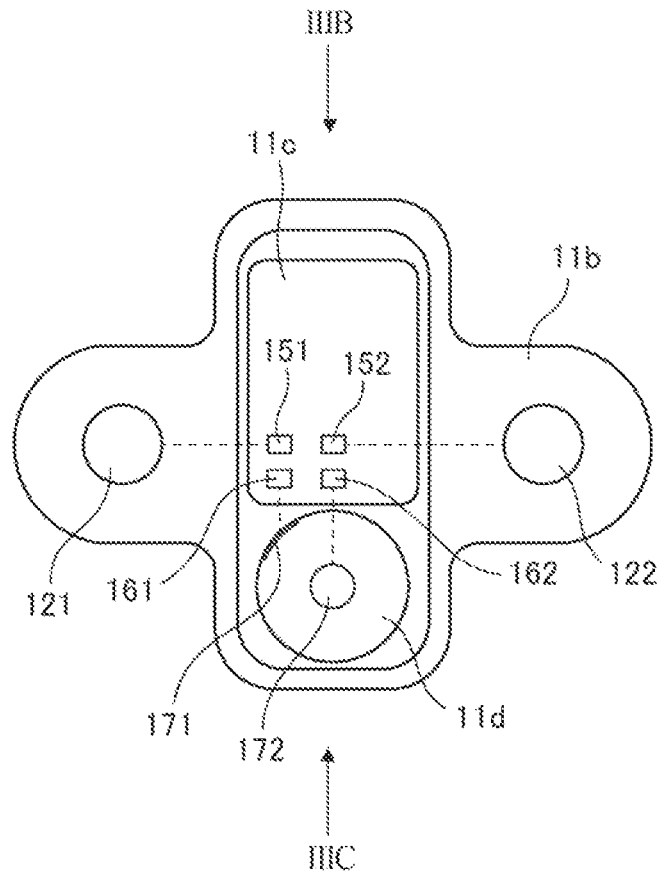
FIGS. 3A to 3C illustrate the configuration of a housing of the sensor of FIG. 1A.
Figure 3B:
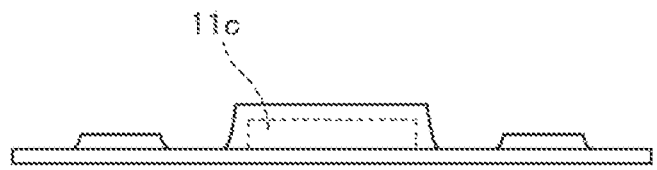
Figure 3C:
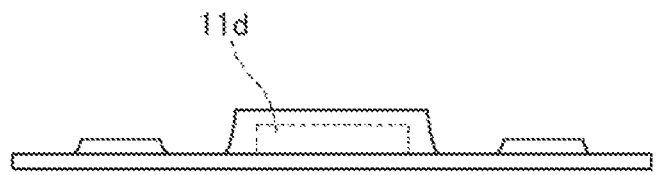

FIG. 3A illustrates the appearance of the sensor 1 in the state where the first cover 131 is detached, FIG. 3B illustrates the appearance of the sensor 1 as seen in the direction of the arrow MB in FIG. 3A, and FIG. 3C illustrates the appearance of the sensor 1 as seen in the direction of the arrow IIIC in FIG. 3A.

The housing 11 may include a module housing member 11c and a battery housing member 11d. The module housing member 11c defines a recess for housing a processor module 7 which will be described later. The battery housing member 11d defines a recess for housing a primary battery 8 which will be described later. The module housing member sic and the battery housing member 11d are covered by the first cover 131 attached to the housing 11.

A first detection terminal 151 and a second detection terminal 152 are disposed in the bottom of the module housing member 11c. The first detection terminal 151 and the second detection terminal 152 are electrically conductive. The first detection terminal 151 is electrically connected to the first electrode 121. The second detection terminal 152 is electrically connected to the second electrode 122.

A first power supply terminal 161 and a second power supply terminal 162 are further disposed in the bottom of the module housing member 11c. The first power supply terminal 161 and the second power supply terminal 162 are electrically conductive.

A positive contact 171 is disposed on the inner side surface of the battery housing member 11d. A negative contact 172 is disposed on the bottom of the battery housing member 11d. The positive contact 171 and the negative contact 172 are electrically conductive. The positive contact 171 is electrically connected to the first power supply terminal 161. The negative contact 172 is electrically connected to the second power supply terminal 162.

Figure 4A:
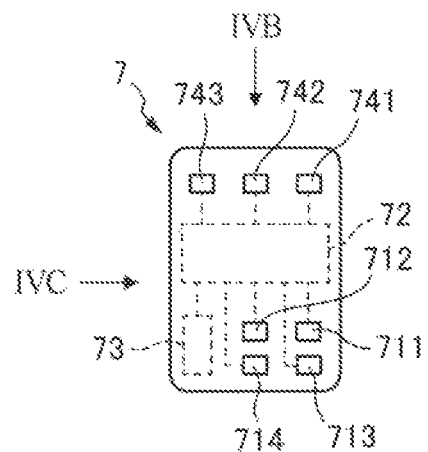
FIGS. 4A to 4C illustrate the configuration of a processor module which is attached to the sensor of FIG. 1A, FIG. 4D and FIG. 4E illustrate the configuration of a primary battery which is attached to the sensor of FIG. 1A.
Figure 4C:
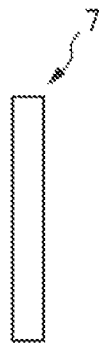
Figure 4D:
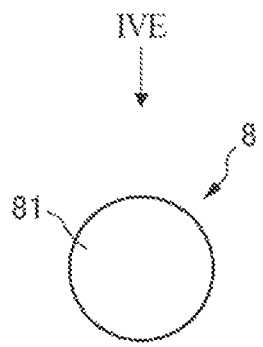
FIG. 4F is a state where the processor module and the primary battery are attached to the housing of FIG. 3A.
Figure 4B:

FIG. 4A illustrates the appearance of the processor module 7, FIG. 4B illustrates the appearance of the processor module 7 as seen in the direction of the arrow IVB in FIG. 4A, and FIG. 4C illustrates the appearance of the processor module 7 as seen in the direction of the arrow IVC in FIG. 4A.

Figure 4E:
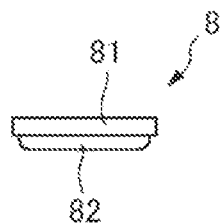

A first detection terminal 711, a second detection terminal 712, a first power supply terminal 713, and a second power supply terminal 714 are disposed on the outer side surface of the processor module 7. The first detection terminal 711, the second detection terminal 712, the first power supply terminal 713, and the second power supply terminal 714 are electrically conductive, FIG. 4(D) illustrates the appearance of the primary battery 8, and FIG. 4(E) illustrates the appearance of the primary battery 8 as seen in the direction of the arrow WE in FIG. 4(D). The primary battery 8 is a so-called button battery. The primary battery 8 has a positive electrode 81 and a negative electrode 82.

Figure 4F:
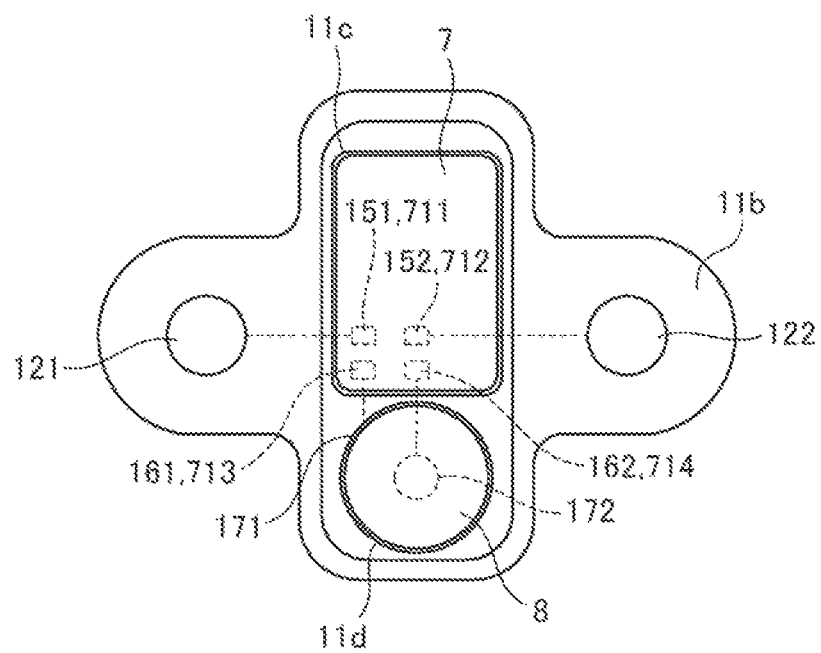

FIG. 4F illustrates the sensor 1 in the state where the processor module 7 is housed in the module housing member 11c, and the primary battery 8 is housed in the battery housing member 11d.

The processor module 7 is housed so that the surface on which the first detection terminal 711, the second detection terminal 712, the first power supply terminal 713, and the second power supply terminal 714 are disposed is opposed to the bottom of the module housing member 11c. The first detection terminal 711 is in contact with the first detection terminal 151, and the second detection terminal 712 is in contact with the second detection terminal 152. Therefore, the first electrode 121 of the housing 11 is electrically connected to the first detection terminal 711 of the processor module 7. In the same or similar manner, the second electrode 122 of the housing 11 is electrically connected to the second detection terminal 712 of the processor module 7.

When the primary battery 8 is housed in the battery housing member 11d, the positive electrode 81 is in contact with the positive contact 171, and the negative electrode 82 is in contact with the negative contact 172. On the other hand, when the processor module 7 is housed in the module housing member 11c, the first power supply terminal 713 is in contact with the first power supply terminal 161, and the second power supply terminal 714 is in contact with the second power supply terminal 162. Therefore, the positive electrode 81 of the primary battery 8 and the first power supply terminal 713 of the processor module 7 are electrically connected to each other. In the same or similar manner, the negative electrode 82 of the primary battery 8 and the second power supply terminal 714 of the processor module 7 are electrically connected to each other.

As illustrated in FIG. 4A, the processor module 7 incorporates a processor 72. The processor 72 is electrically connected to the first power supply terminal 713 and the second power supply terminal 714. The processor 72 operates with a power supply from the primary battery 8 through the first power supply terminal 713 and the second power supply terminal 714.

On the other hand, the processor 72 is communicably connected to the first detection terminal 711 and the second detection terminal 712 through an interface which is not illustrated. The biopotential which is detected by the first electrode 121, and which is then supplied to the first detection terminal 711 is set to a state where the biopotential can be processed by the processor 72, by an adequate circuit configuration included in the interface. Also the biopotential which is detected by the second electrode 122, and which is then supplied to the second detection terminal 712 is set to a state where the biopotential can be processed by the processor 72, by an adequate circuit configuration included in the interface.

The processor 72 is configured so as to acquire physiological information of the subject S based on information corresponding to the biopotential which are supplied to the first detection terminal 711 and the second detection terminal 712. Specifically, information of the motion of the heart of the subject S is acquired based on temporal changes of the information corresponding to the biopotential. Examples of the information are the heart rate, ventricular fibrillation, ventricular tachycardia, and cardiac standstill.

The above-described function of the processor 72 may be realized by a general-purpose microprocessor which operates in cooperation with a memory, or by a dedicated integrated circuit such as a microcomputer, an ASIC, or an FPGA.

As illustrated in FIG. 4A, the processor module 7 may include a wireless communication device 73. In the configuration, the physiological information of the subject S which is acquired by the processor 72 can be wirelessly transmitted to a remote device by the wireless communication device 73. Examples of such a remote device are a device which can visualize the physiological information, and that which can perform notification based on the physiological information.

The processor module 7 may include a storage device which is not illustrated, in place of the wireless communication device 73. In this case, the physiological information of the subject S which is acquired by the processor 72 can be stored in the storage device without being subjected to wireless transmission. The physiological information stored in the storage device can be thereafter read therefrom in contact or non-contact communication. Therefore, the processor module 7 may include as necessary terminals for reading physiological information.

As illustrated in FIGS. 3A and 4F, the processor module 7 is attachable to and detachable from the housing 11 independently of the primary battery 8. According to the configuration, the processor module 7 can be shared among a plurality of kinds of sensor housings which are adaptable to modes of acquiring various physiological information that will be described later. The processor module 7 is attached to a sensor housing which is suitable to the mode of acquiring physiological information to be obtained, whereby various use environments can be provided to the user. Moreover, it is not required to dispose a processor for each of sensor housings, and therefore the operational cost can be suppressed from being raised.

Other advantages of the sensor 1 will be described before description of other embodiments of the sensor housing.

Figure 5A:
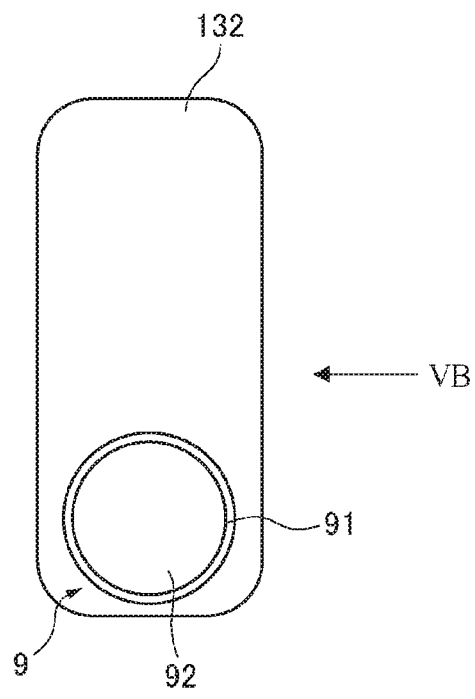
FIGS. 5A and 5B illustrate the configuration of a second cover which is attached to the housing of FIG. 3A.
Figure 5B:
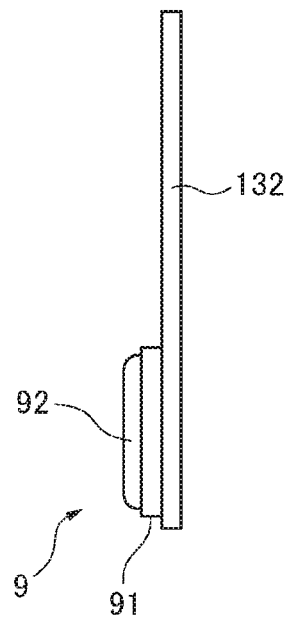

FIG. 5A illustrates the appearance of a second cover 132 which can be attached to the housing 11, and FIG. 5B illustrates the appearance of the second cover 132 as seen in the direction of the arrow VB in FIG. 5A.

The second cover 132 can be attached to the housing 11 in place of the first cover 131. The second cover 132 which is attached to the housing 11 covers the module housing member 11c and the battery housing member 11d. A secondary battery 9 is disposed integrally with the second cover 132. The secondary battery 9 has the same shape as the primary battery 8, and has a positive electrode 91 and a negative electrode 92.

The secondary battery 9 is configured so as to be rechargeable. The secondary battery 9 may undergo a contact charging process by using a charge device which includes power supply terminals that are to be connected to the positive electrode 91 and the negative electrode 92, respectively, or incorporate a power supply antenna in the second cover 132 so as to be subjected to a non-contact charging operation.

When the second cover 132 is attached to the housing 11, the secondary battery 9 is housed in the battery housing member 11d. When the secondary battery 9 is housed in the battery housing member 11d, the positive electrode 91 is in contact with the positive contact 171, and the negative electrode 92 is in contact with the negative contact 172. Therefore, the positive electrode 91 of the secondary battery 9 and the first power supply terminal 713 of the processor module 7 are electrically connected to each other. In the same or similar manner, the negative electrode 92, of the secondary battery 9 and the second power supply terminal 714 of the processor module 7 are electrically connected to each other. The processor 72 operates with a power supply from the secondary battery 9 through the first power supply terminal 713 and the second power supply terminal 714.

According to the configuration, the primary battery 8 and the secondary battery 9 can be selectively used, and the user can be provided with a use environment having a high degree of freedom. Particularly, the secondary battery 9 is disposed integrally with the second cover 132 and therefore the risk of losing the secondary battery 9 in a situation where a cycle of use and recharge is repeated can be reduced.

In the same or similar manner as the processor module 7, preferably, the second cover 132 is configured with a specification in which the second cover can be attached to a plurality of kinds of sensor housings that are adaptable to modes of acquiring various physiological information which will be described later.

In the sensor 1 of the embodiment, the first electrode 121 and the second electrode 122 are supported by the housing 11.

According to the configuration, simply when the housing 11 is attached to the body of the subject S, it is possible to attain a state where desired physiological information can be acquired. Moreover, the relative position between the first electrode 121 and the second electrode 122 is unchanged, and therefore a stable detection state is easily ensured.

As described above, the housing 11 is attached to the subject S so that the lower surface 11*b* is opposed to the skin of the subject. The lower surface 11*b* is an example of the attachment surface. As illustrated in FIG. 3A, the module housing member 11*c* and the battery housing member 11*d* are opened in the lower surface 11*b*. Namely, the first cover 131 or the second cover 132 is attached to the side on the side of the lower surface 11*b*.

According to the configuration, the module housing member 11*c* and the battery housing member 11*d* are covered by the first cover 131 or the second cover 132, and the sensor 1 is attached to the subject S in a state where the first cover 131 or the second cover 132 is covered by the housing 11. During a use of the sensor 1, therefore, it is easy to ensure waterproofness to the processor module 7 housed in the module housing member 11*c*, and also to the primary battery 8 or secondary battery 9 housed in the battery housing member 11*d*.

Figure 6:
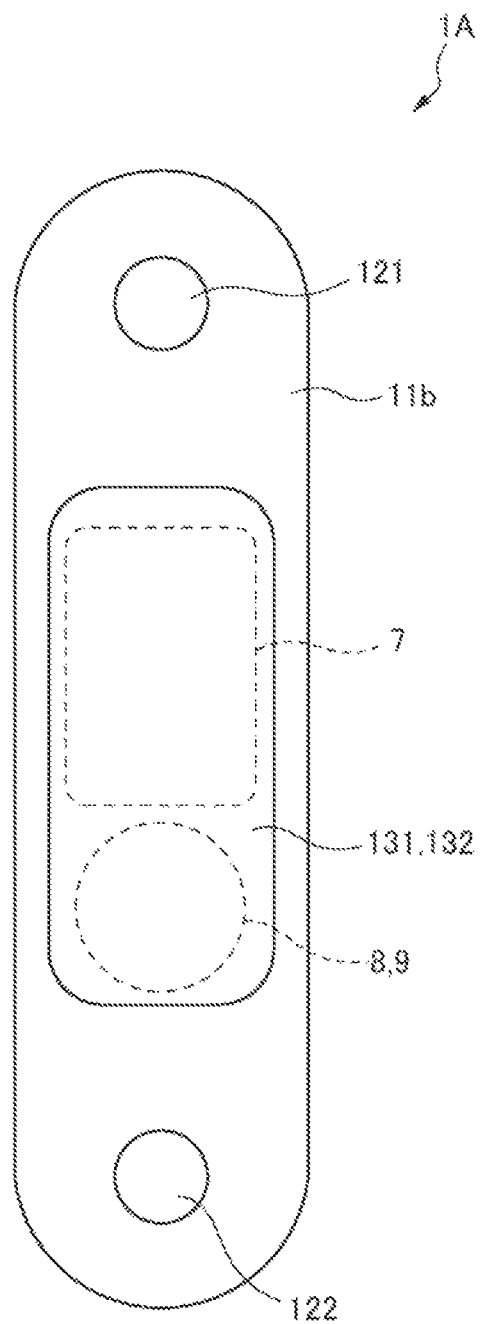
FIG. 6 illustrates a first modification of the sensor of FIG. 7A.
Figure 7:
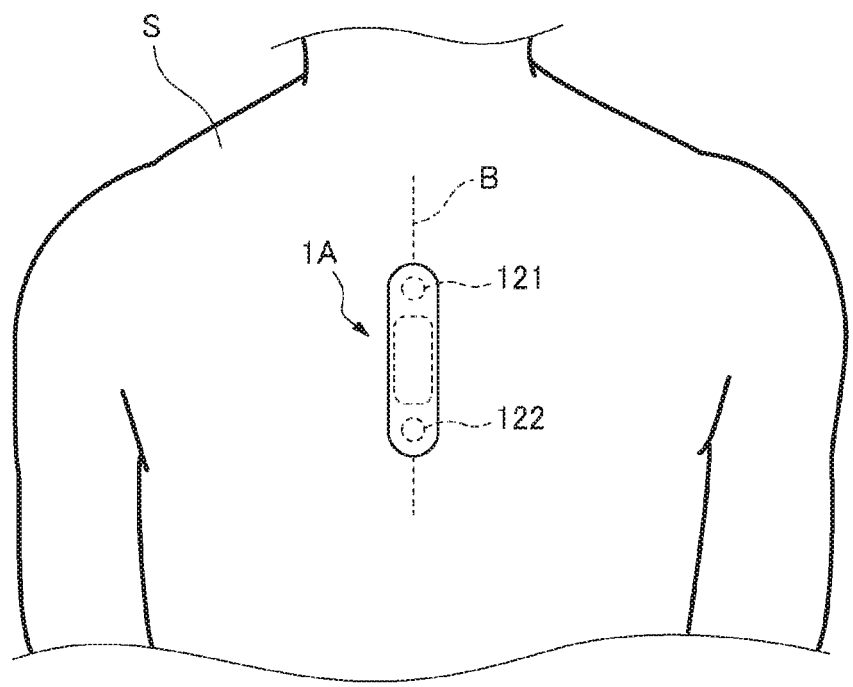
FIG. 7 illustrates a position where the sensor of FIG. 6 is attached.

FIG. 6 illustrates the appearance of a sensor 1A of a first modification as seen from the side of the lower surface 11*b*. The sensor 1A is attached to the subject S as illustrated in FIG. 7. In the modification, the first electrode 121 and the second electrode 122 are supported by the housing 11 so as to be arranged along the breastbone B of the subject S.

According to the configuration, the first electrode 121 and the second electrode 122 are arranged along the breastbone B which is harder than the circumference, and therefore positional displacements of the first electrode 121 and the second electrode 122 during the use are caused to hardly occur. In the case where the subject S is a female, particularly, it is possible to suppress the mamma from influencing the acquisition of physiological information. When the distance between the first electrode 121 and the second electrode 122 is adequately set, moreover, the NASA lead waveform can be acquired in addition to the above-mentioned information relating to the motion of the heart.

Figure 8:
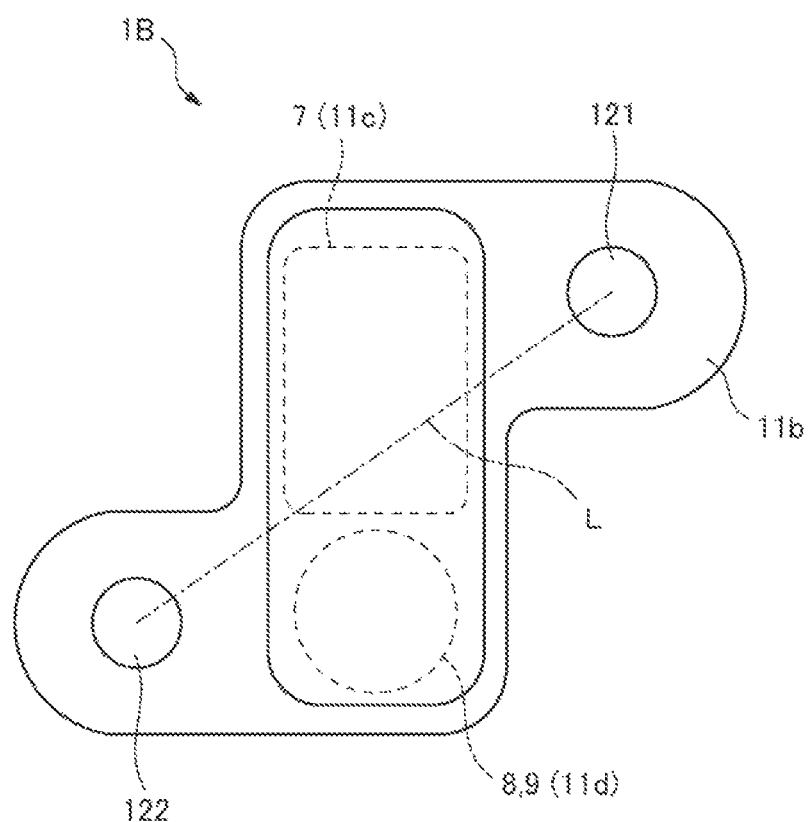
FIG. 8 illustrates a second modification of the sensor of FIG. 1A.
Figure 9:
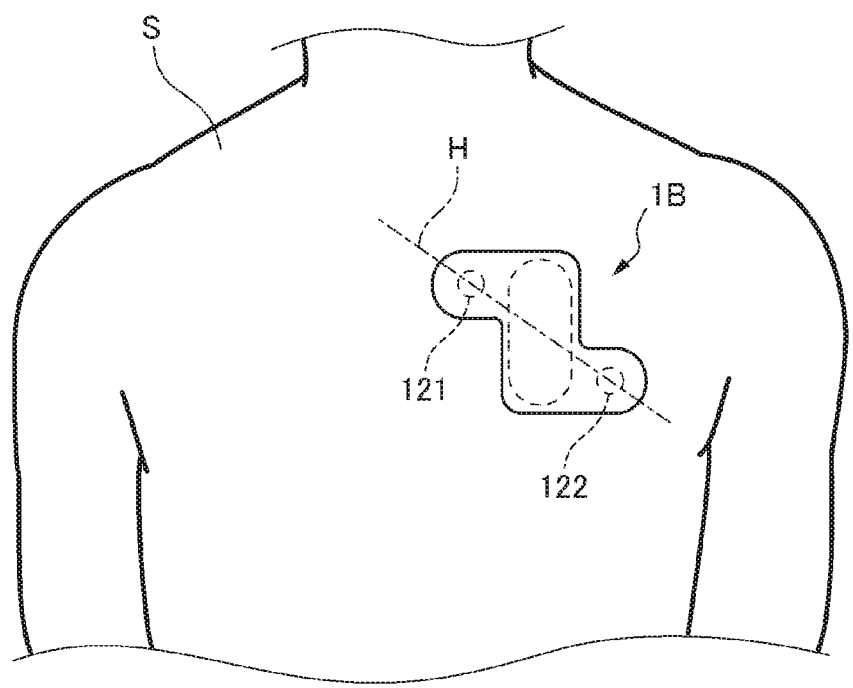
FIG. 9 illustrates a position where the sensor of FIG. 8 is attached.

FIG. 8 illustrates the appearance of a sensor 1B of a second modification as seen from the side of the lower surface 11*b*. The sensor 1B is attached to the subject S as illustrated in FIG. 9. In the modification, the first electrode 121 and the second electrode 122 are supported by the housing 11 so that a straight line L connecting their middles obliquely crosses the module housing member 11*c*. The first electrode 121 and the second electrode 122 may be placed so that the straight line L obliquely crosses at least one of the module housing member 11*c* and the battery housing member 11*d*.

According to the configuration, as illustrated in FIG. 9, the sensor 1B can be attached to the subject S so that the first electrode 121 and the second electrode 122 are arranged along the heart electrical axis H of the subject. In this case, particularly, the detection of the R wave in an electrocardiogram waveform is easily optimized.

Figure 10A:
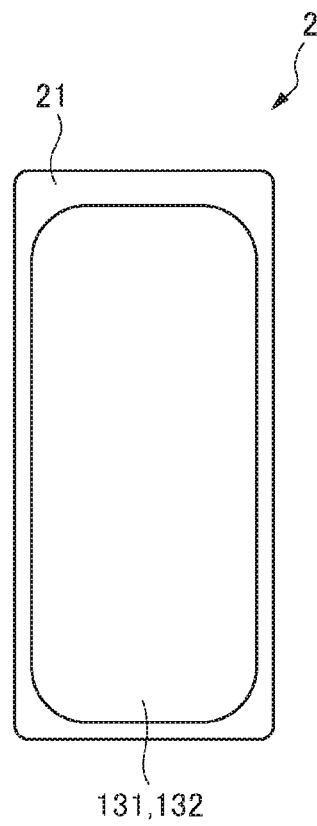
FIGS. 10A to 10C illustrate the configuration of a sensor of a second embodiment.

FIG. 10A illustrates the appearance of a sensor 2 of a second embodiment. The constituting elements which are substantially identical with those of the sensor 1 of the first embodiment are denoted by the same reference numerals, and repeated description is omitted.

Figure 10B:
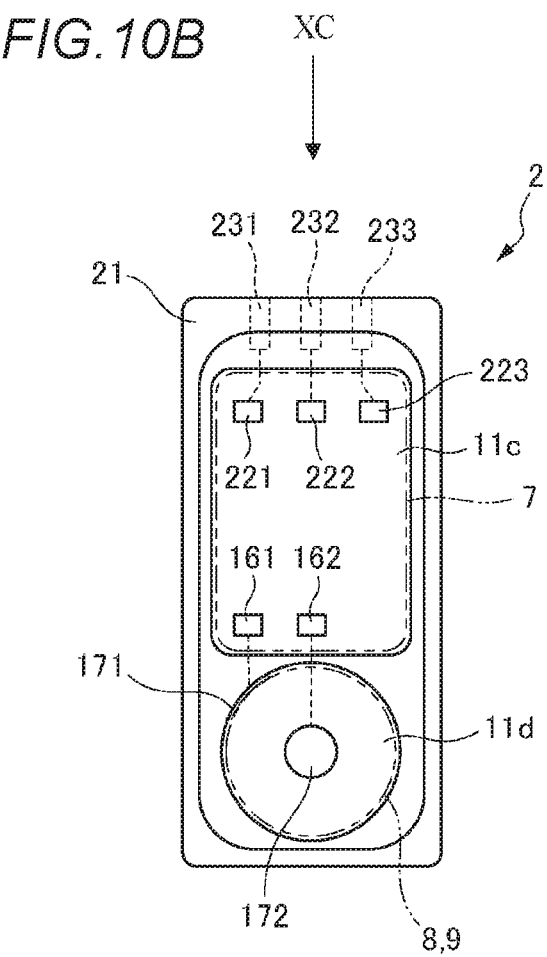

The sensor 2 may include a housing 21. The first cover 131 or the second cover 132 is attached to the housing 21. FIG. 10B illustrates the appearance of the sensor 2 in the state where the first cover 131 or the second cover 132 is detached from the housing. The housing 21 may include the module housing member 11*c* and the battery housing member 11*d*. The module housing member 11*c* and the battery housing member 11*d* are covered by the first cover 131 or second cover 132 which is attached to the housing 21.

A first lead terminal 221, a second lead terminal 222, and a third lead terminal 223 are disposed on the bottom of the module housing member 11*c*, in addition to the first power supply terminal 161 and the second power supply terminal 162. The first lead terminal 221, the second lead terminal 222, and the third lead terminal 223 are electrically conductive.

Figure 10C:
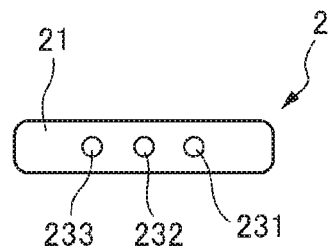

FIG. 10C illustrates the appearance of the sensor 2 as seen in the direction of the arrow XC in FIG. 10B. The sensor 2 may include a first connection terminal 231, a second connection terminal 232, and a third connection terminal 233. The first connection terminal 231, the second connection terminal 232, and the third connection terminal 233 are electrically conductive. The first connection terminal 231 and the first lead terminal 221 are electrically connected to each other. The second connection terminal 232 and the second lead terminal 222 are electrically connected to each other. The third connection terminal 233 and the third lead terminal 223 are electrically connected to each other.

Figure 11:
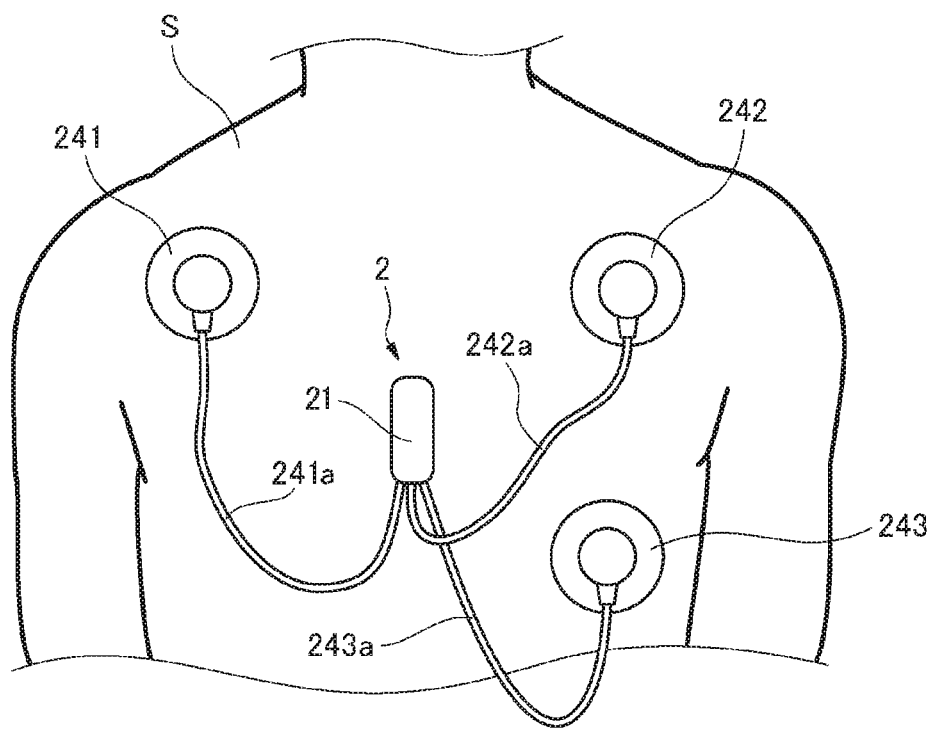
FIG. 11 illustrates a usage mode of the sensor of FIG. 10A.

As illustrated in FIG. 11, the sensor 2 may include a first lead electrode 241, a second lead electrode 242, and a third lead electrode 243. The first lead electrode 241, the second lead electrode 242, and the third lead electrode 243 are electrically conductive. The first lead electrode 241, the second lead electrode 242, and the third lead electrode 243 are connected to the housing 21.

The first lead electrode 241 is attached to, for example, the right subclavian area of the subject S to detect the biopotential of the area. The first lead electrode 241 is connected to the first connection terminal 231 illustrated in FIG. 10B, through a flexible signal line 241*a* illustrated in FIG. 11.

The second lead electrode 242 is attached to, for example, the left subclavian area of the subject S to detect the biopotential of the area. The second lead electrode 242 is connected to the second connection terminal 232 illustrated in FIG. 10B, through a flexible signal line 242*a* illustrated in FIG. 11.

The third lead electrode 243 is attached to, for example, the left lower chest area of the subject S to detect the biopotential of the area. The third lead electrode 243 is connected to the third connection terminal 233 illustrated in FIG. 10B, through a flexible signal line 243*a* illustrated in FIG. 11.

As illustrated in FIG. 4A, a first lead terminal 741, a second lead terminal 742, and a third lead terminal 743 are disposed on the outer side surface of the processor module 7. The first lead terminal 741, the second lead terminal 742, and the third lead terminal 743 are electrically conductive.

The processor module 7 is housed in the module housing member 11*c* so that the surface on which the first lead terminal 741, the second lead terminal 742, and the third lead terminal 743 are disposed is opposed to the bottom of the module housing member 11*c*. The first lead terminal 741 is in contact with the first lead terminal 221. The second lead terminal 742 is in contact with the second lead terminal 222. The third lead terminal 743 is in contact with the third lead terminal 223.

Therefore, the first lead electrode 241 and the first lead terminal 741 of the processor module 7 are electrically connected to each other. In the same or similar manner, the second lead electrode 242 and the second lead terminal 742 of the processor module 7 are electrically connected to each other, and the third lead electrode 243 and the third lead terminal 743 of the processor module 7 are electrically connected to each other.

As illustrated in FIG. 4A, the processor 72 of the processor module 7 is communicably connected to the first lead terminal 741, the second lead terminal 742, and the third lead terminal 743 through an interface which is not illustrated. The biopotential which is detected by the first lead electrode 241, and which is then supplied to the first lead terminal 741 is set to a state where the biopotential can be processed by the processor 72, by an adequate circuit configuration included in the interface. The biopotential which is detected by the second lead electrode 242, and which is then supplied to the second lead terminal 742 is set to a state where the biopotential can be processed by the processor 72, by an adequate circuit configuration included in the interface. The biopotential which is detected by the third lead electrode 243, and which is then supplied to the third lead terminal 743 is set to a state where the biopotential can be processed by the processor 72, by an adequate circuit configuration included in the interface.

The processor 72 is caused to operate by the electric power which is supplied from the primary battery 8 or secondary battery 9 that is housed in the battery housing member 11d. The processor 72 is configured so as to acquire physiological information of the subject S based on information corresponding to the biopotential which are supplied to the first lead terminal 741, the second lead terminal 742, and the third lead terminal 743, respectively.

For example, the I lead waveform in an electrocardiogram is acquired based on the temporal change of the biopotential which is detected by the first lead electrode 241, and that of the biopotential which is detected by the second lead electrode 242. For example, the II lead waveform in an electrocardiogram is acquired based on the temporal change of the biopotential which is detected by the first lead electrode 241, and that of the biopotential which is detected by the third lead electrode 243. For example, the III lead waveform in an electrocardiogram is acquired based on the temporal change of the biopotential which is detected by the second lead electrode 242, and that of the biopotential which is detected by the third lead electrode 243. When the attachment positions of the first lead electrode 241, the second lead electrode 242, and the third lead electrode 243 are appropriately changed, also the MCL1 and MCL5 lead waveforms and the like in an electrocardiogram can be acquired.

In the embodiment, the first lead electrode 241, second lead electrode 242, and third lead electrode 243 which are to be attached to the subject S are connected to the housing 21 through the flexible signal lines 241a, 242a, 243a, respectively. Therefore, the detection positions of the biological electrodes can be correctly ensured irrespective of the body shape of the subject S. The attachment positions of the electrodes are easily changed in accordance with the type of the physiological information (lead waveform) to be acquired. When the first lead electrode 241, the second lead electrode 242, and the third lead electrode 243 are disposal for every subject, moreover, the housing 21 can be continuously reused.

When physiological information is to be acquired by using the first lead electrode 241, the second lead electrode 242, and the third lead electrode 243, the housing 21 may be attached to the chest of the subject S through an adhesive agent, in this case, preferably, the housing 21 is attached to the chest so that the side of the housing to which the first cover 131 or the second cover 132 is attached is opposed to the skin of the subject S.

Figure 12:
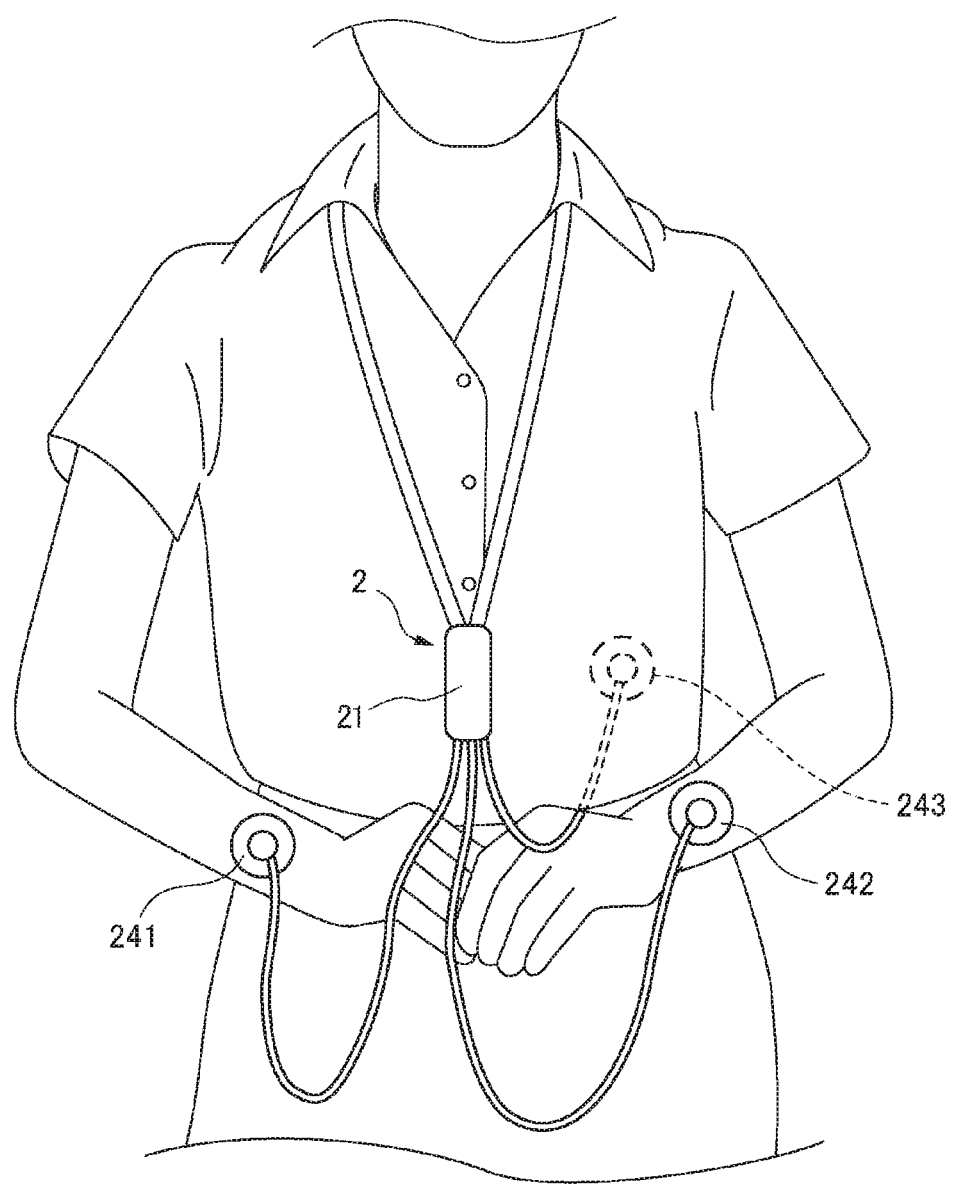
FIG. 12 illustrates another usage mode of the sensor of FIG. 10A.
Figure 13:
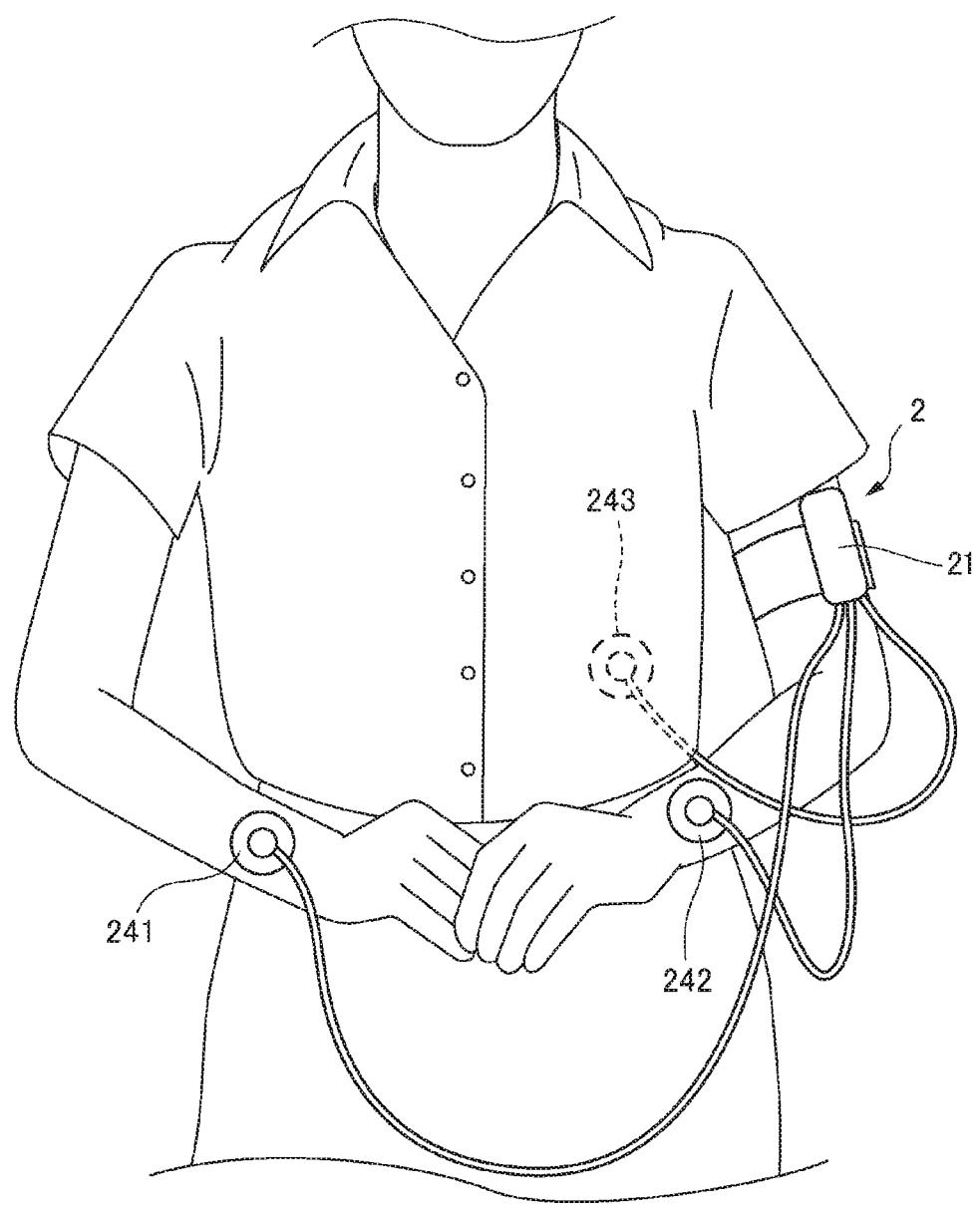
FIG. 13 illustrates a further usage mode of the sensor of FIG. 10A.

As illustrated in FIG. 12, alternatively, the housing 21 may be carried while the housing is hung from the neck of the subject S via a strap. As illustrated in FIG. 13, alternatively, the housing 21 may be fixed to the body of the subject S via a holder.

In the example illustrated in FIG. 11, the first lead electrode 241, the second lead electrode 242, and the third lead electrode 243 are attached to the periphery of the chest of the subject S. In this case, the subject S inevitably gets undressed. However, there may be a situation where the subject S has strong feelings of resistance to undressing (for example, in the case where the subject S is female, and an electrocardiogram must be acquired during dental treatment). FIGS. 12 and 13 illustrate use examples of the sensor 2 in which an electrocardiogram can be acquired without undressing.

In these examples, the first lead electrode 241 is attached to the left wrist or left upper arm of the subject S, the second lead electrode 242 is attached to the right wrist or tight upper arm of the subject 5, and the third lead electrode 243 is attached to the right ankle (in this case, undressing is unnecessary) or tight flank (in this case, only minimum undressing is necessary). Also in such an electrode arrangement, the above-described I, II, and III leads can be acquired.

The sensor 2 may have a configuration in which the third lead electrode 243 is not used. In this case, although the number of leads which can be acquired is reduced, undressing can be made completely unnecessary.

In the case where the housing 21 is placed on the outside of the clothes, the housing 21 may be fixed to the clothes through a clip or the like, or carried in a pocket of the clothes, in place of the examples illustrated in FIGS. 12 and 13.

FIG. 14A illustrates the appearance of a sensor 3 of a third embodiment. The constituting elements which are substantially identical with those of the sensor 2 of the second embodiment are denoted by the same reference numerals, and repeated description is omitted.

The sensor 3 may include a housing 31. The first cover 131 or the second cover 132 is attached to the housing 31. FIG. 14B illustrates the appearance of the sensor 3 in the state where the first cover 131 or the second cover 132 is detached from the housing. The housing 31 may include the module housing member 11c and the battery housing member 11d. The module housing member 11c and the battery housing member 11d are covered by the first cover 131 or second cover 132 which is attached to the housing 31.

The sensor 3 may include a first connection terminal 331, a second connection terminal 332, and a third connection terminal 333. The first connection terminal 331 and the first lead terminal 221 are electrically connected to each other. The second connection terminal 332 and the second lead terminal 222 are electrically connected to each other. The third connection terminal 333 and the third lead terminal 223 are electrically connected to each other.

Figure 15:
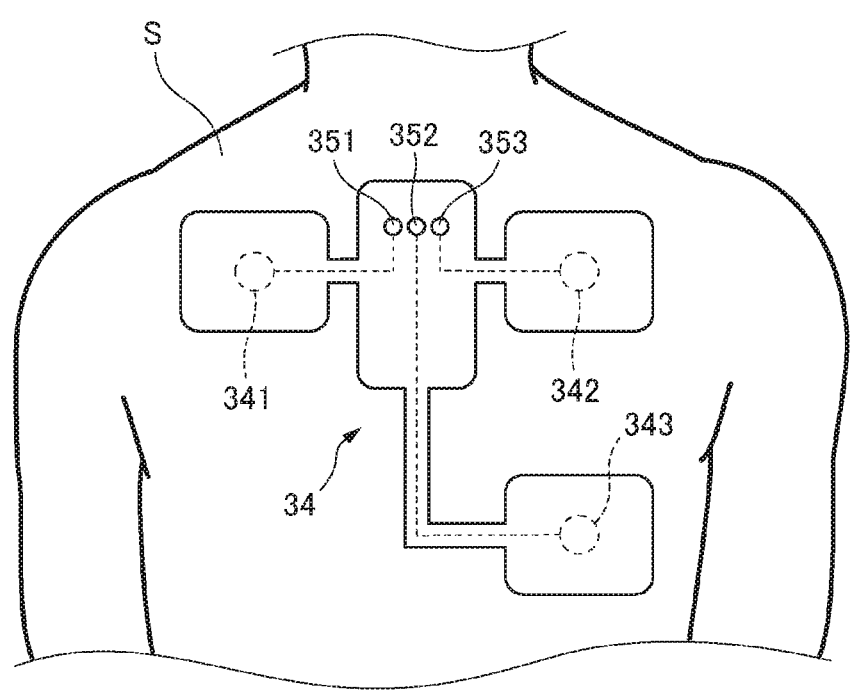
FIG. 15 illustrates the configuration of an electrode pad to which the housing of FIG. 14A is attached.

As illustrated in FIG. 15, the sensor 3 may include an electrode pad 34. The electrode pad 34 supports a first lead electrode 341, a second lead electrode 342, and a third lead electrode 343. The electrode pad 34 is attached to the chest of the subject S through an adhesive agent. The electrode pad 34 has a shape in which the first lead electrode 341 is to be placed in the right subclavian area of the subject S, the second lead electrode 342 is to be placed in the left subclavian area of the subject S, and the third lead electrode 343 is to be placed in the left lower chest area of the subject S.

The electrode pad 34 further supports a first connection terminal 351, a second connection terminal 352, and a third connection terminal 353. The first connection terminal 351, the second connection terminal 352, and the third connection terminal 353 are electrically conductive. The first connection terminal 351 is electrically connected to the first lead electrode 341. The second connection terminal 352 is electrically connected to the second lead electrode 342. The third connection terminal 353 is electrically connected to the third Lead electrode 343.

The housing 31 is attached to the electrode pad 34. Specifically, the first connection terminal 331, second connection terminal 332, and third connection terminal 333 of the housing 31 are coupled to the first connection terminal 351, second connection terminal 352, and third connection terminal 353 of the electrode pad 34, respectively, whereby the attachment is performed. Each of the pairs of the first connection terminal 331 and the first connection terminal 351, the second connection terminal 332 and the second connection terminal 352, and the third connection terminal 333 and the third connection terminal 353 may be configured as a combination of convex and concave members which constitutes, for example, a snap-fit joint.

When the housing 31 is attached to the electrode pad 34, the first lead electrode 341 and the first lead terminal 741 of the processor module 7 are electrically connected to each other. In the same or similar manner, the second lead electrode 342 and the second lead terminal 742 of the processor module 7 are electrically connected to each other. In the same or similar manner, the third lead electrode 343 and the third lead terminal 743 of the processor module 7 are electrically connected to each other.

The processor 72 is caused to operate by the electric power which is supplied from the primary battery 8 or secondary battery 9 that is housed in the battery housing member 11d. The processor 72 is configured so as to acquire physiological information of the subject S based on information corresponding to the biopotential which are supplied to the first lead terminal 741, the second lead terminal 742, and the third lead terminal 743, respectively.

For example, the I lead waveform in an electrocardiogram is acquired based on the temporal change of the biopotential which is detected by the first lead electrode 341, and that of the biopotential which is detected by the second lead electrode 342. For example, the II lead waveform in an electrocardiogram is acquired based on the temporal change of the biopotential which is detected by the first lead electrode 341, and that of the biopotential which is detected by the third lead electrode 343. For example, the III lead waveform in an electrocardiogram is acquired based on the temporal change of the biopotential which is detected by the second lead electrode 342, and that of the biopotential which is detected by the third lead electrode 343.

According to the configuration, only the electrode pad 34 may be disposal for every subject 5, and the housing 31 may be continuously reused. Moreover, the relative positions between the first lead electrode 341, the second lead electrode 342, and the third lead electrode 343 are unchanged, and therefore a stable detection state is easily ensured.

The sensors 1, 1A, 2, 3 which have been described above include the sensor housings having the different specifications, respectively, and also their modes of acquiring physiological information are different from one another. However, the processor module 7 can be shared among a plurality of kinds of sensor housings, and therefore a wide variety of use environments can be provided to the user while suppressing the operational cost from being raised.

Moreover, the specification of a sensor housing, and the mode of acquiring physiological information may be changed in accordance with the physical feature (the age, the sex, the physical size, the race, handicapped or non-handicapped, etc.) of the subject S to whom the sensor housing is to be attached. However, the processor module 7 can be shared among a plurality of kinds of sensor housings, and therefore the common function of the processor module 7 can be provided to a plurality of users having various physical features, while suppressing the operational cost from being raised.

Moreover, the processor module 7 can be made attachable to and detachable from the sensor housing independently of the primary battery 8 or the secondary battery 9. Even when the specification of the sensor housing is changed from the viewpoint of the battery life, therefore, it is possible to flexibly cope with the change. Even in a sensor housing in which the configuration of the battery housing member 11d is changed so as to be able to house a large-capacity or large-size battery having a longer life battery while maintaining the configuration of the module housing member 11c, for example, the processor module 7 cab be used commonly without changing the specification.

The above-described embodiments are mere examples for facilitating understanding of the disclosure. The configuration of the embodiments may be adequately changed or improved without departing from the spirit of the presently disclosed subject matter.

In the above-described embodiments, the first cover 131 or the second cover 132 covers both the module housing member 11c and the battery housing member 11d. However, the module housing member 11c is not always required to be formed as a recess which is opened in the same direction as the battery housing member 11d. For example, a slot into and from which the processor module 7 is insertable and extractable may be formed in the sensor housing. In this case, the module housing member 11c may be formed in the sensor housing, as a space which communicates with the slot, and the first cover 131 or the second cover 132 may be configured so as to cover at least the battery housing member 11d.

The number and arrangement of each of the various kinds of terminals which are disposed in the processor module 7 may be appropriately determined in accordance with the number of used electrodes and the specification of the module housing member 11c.

A motion sensor may be incorporated in the processor module 7. The motion sensor detects the attitude and body motion of the subject S, and may be realized by an acceleration sensor or a gyroscope sensor. In this case, preferably, the module housing members 11c of the sensors which have been described above are configured so that the processor modules 7 that are attached to the housing are oriented in the same direction. According to the configuration, in the case where the processor module 7 is shared among a plurality of sensors having different specifications, detection results which are output from the motion sensor can be easily handled.

The configuration of each of the primary battery 8 and the secondary battery 9 is not particularly limited to a button battery, and may be adequately determined as far as the shape is common to the batteries.

What is claimed is:

1. A sensor comprising:
a plurality of electrodes configured to be attached to a subject;
a processor module which acquires physiological information of the subject based on biopotential that are detected by each of the plurality of electrodes;
a housing comprising:
an attachment surface configured to be attached to the subject,
a module housing member for housing the processor module, and
a battery housing member for housing a battery which supplies an electric power to the processor module; and
a cover attachable to the housing, wherein the processor module is attachable to and detachable from the housing separately and independently from the battery,
wherein the cover is configured to cover the battery housing member when the cover is attached to the housing,
wherein the module housing member defines a first opening for housing the processor module, and the battery housing member defines a second opening for housing the battery, and
wherein each of the first opening and the second opening is a discrete opening that begins at the attachment surface and extends away from the attachment surface.

2. The sensor according to claim 1, wherein the battery is a primary battery.

3. The sensor according to claim 2, wherein the plurality of electrodes are supported by the housing.

4. The sensor according to claim 3, wherein the plurality of electrodes are supported by the housing so as to be configured to be arranged along a breastbone of the subject.

5. The sensor according to claim 3, wherein the cover is attached to the attachment surface.

6. The sensor according to claim 2, wherein at least one of the plurality of electrodes is connected to the housing through a flexible signal line.

7. The sensor according to claim 1, the battery is a secondary battery which is housed in the battery housing member, and the secondary battery is disposed integrally with the cover.

8. The sensor according to claim 1, wherein the battery housing member and the module housing member are arranged so as not to overlap each other when viewed from a side of the attachment surface.

9. The sensor according to claim 1, wherein the module housing member and the battery housing member are exposed next to each other at the attachment surface.

10. The sensor according to claim 1, wherein the cover is configured to cover the module housing member.

11. A processor module which acquires physiological information of a subject based on biopotential detected by each of a plurality of electrodes attached to the subject,
wherein the processor module receives a power supply from a battery housed in a battery housing member of a housing having an attachment surface configured to be attached to the subject,
wherein the processor module is housed in a module housing member of the housing, and is attachable to and detachable from the housing separately and independently from the battery, and
wherein a cover attached to the housing covers the battery housing member,
wherein the module housing member defines a first opening for housing the processor module, and the battery housing member defines a second opening for housing the battery, and
wherein each of the first opening and the second opening is a discrete opening that begins at the attachment surface and extends away from the attachment surface.

12. A sensor housing comprising:
a battery housing member for housing a battery which supplies an electric power to a processor module for acquiring physiological information of a subject based on biopotential detected by each of a plurality of electrodes attached to the subject;
a module housing member for housing the processor module; and
an attachment surface configured to be attached to the subject,
wherein the processor module is attachable to and detachable from the sensor housing separately and independently from the battery housing member, and
wherein a cover attached to the sensor housing covers the battery housing member, and
wherein the module housing member defines a first opening for housing the processor module, and the battery housing member defines a second opening for housing the battery, and
wherein each of the first opening and the second opening is a discrete opening that begins at the attachment surface and extends away from the attachment surface.

* * * * *